United States Patent [19]
D'Arrigo

[11] Patent Number: 5,215,680
[45] Date of Patent: Jun. 1, 1993

[54] METHOD FOR THE PRODUCTION OF MEDICAL-GRADE LIPID-COATED MICROBUBBLES, PARAMAGNETIC LABELING OF SUCH MICROBUBBLES AND THERAPEUTIC USES OF MICROBUBBLES

[75] Inventor: Joseph S. D'Arrigo, Farmington, Conn.

[73] Assignee: Cavitation-Control Technology, Inc., Farmington, Conn.

[21] Appl. No.: 550,620

[22] Filed: Jul. 10, 1990

[51] Int. Cl.$^5$ ............... B01J 13/00; A61K 49/00; A61K 9/107; B01F 3/04
[52] U.S. Cl. .................. 252/307; 424/2; 424/9; 436/173; 128/662.02; 128/653.4; 514/938; 252/314
[58] Field of Search ............ 424/9; 436/173; 128/662.02

[56] References Cited

U.S. PATENT DOCUMENTS

| | | | |
|---|---|---|---|
| 4,276,885 | 7/1981 | Tickner et al. | 128/660 |
| 4,466,442 | 8/1984 | Hilmann et al. | 128/660 X |
| 4,572,203 | 2/1986 | Feinstein | 128/661 |
| 4,684,479 | 8/1987 | D'Arrigo | 252/307 |
| 4,774,958 | 10/1988 | Feinstein | 128/660 |
| 4,832,941 | 5/1989 | Berwing et al. | 424/9 |
| 4,900,540 | 2/1990 | Ryan et al. | 424/9 |
| 4,927,637 | 5/1990 | Morano et al. | 424/450 |
| 4,985,233 | 1/1991 | Klaveness et al. | 424/9 |
| 5,078,986 | 1/1992 | Bosworth et al. | 424/9 |
| 5,088,499 | 2/1992 | Unger | 424/9 X |

OTHER PUBLICATIONS

Carr et al, "Intravenous Chelated Gadolinium As A Contrast Agent In NMR Imaging Of Cerebral Tumors", *Lancet*, pp. 484–486 (Mar. 3, 1984).

Lauffer et al, "Preparation and Water Relaxation Properties of Proteins Labeled with Paramagnetic Metal Chelates", *Mag. Res. Imaging*, 3:11–16 (1985).

Lauffer et al, "1/$T_1$ NMRD Profiles of Solutions of $Mn^{2+}$ and $Gd^{3+}$ Protein-Chelate Conjugates", *Mag. Res. Med.*, 3:541–548 (1986).

Quan et al, "Applicators for generating ultrasound-induced hyperthermia in neoplastic tumours and for use in ultrasound physiotherapy", *Phys. Med. Biol.*, 34:1719–1731 (1989).

Runge et al, "Initial Clinical Evaluation of Gadolinium DTPA For Contrast-Enhanced Magnetic Resonance Imaging", *Mag. Res. Imaging*, 3:27–35 (1985).

ter Haar et al, "High intensity focused ultrasound—a surgical technique for the treatment of discrete liver tumours", *Phys. Med. Biol.*, 34:1743–50 (1989).

Primary Examiner—Richard D. Lovering
Assistant Examiner—John M. Covert
Attorney, Agent, or Firm—Kramer, Brufsky & Cifelli

[57] ABSTRACT

This invention relates to a large scale method for the production of medical grade lipid-coated microbubbles, to the paramagnetic labeling of such microbubbles and to therapeutic applications for the microbubbles. More particularly, the invention relates to a method of the production of medical grade, concentrated suspensions of stable, paramagnetically derivatized or underivatized microbubbles useful for ultrasonic and magnetic resonance imaging and also relates to therapeutic interventions such as selective tumor destruction.

10 Claims, 4 Drawing Sheets

METHOD FOR THE PRODUCTION OF MEDICAL-GRADE LIPID-COATED MICROBUBBLES, PARAMAGNETIC LABELING OF SUCH MICROBUBBLES AND THERAPEUTIC USES OF MICROBUBBLES

This invention was made with Government support under SBIR Phase II Grant No. 2 R44 NS25851-02 awarded by the National Institute of Neurological Disorders and Stroke, National Institutes of Health. The Government has certain rights in the invention.

FIELD OF THE INVENTION

This invention relates to methods for the production of medical grade lipid-coated microbubbles, to the paramagnetic labeling of such microbubbles and to therapeutic applications for the microbubbles. More particularly, the invention relates to methods for the production of medical grade, concentrated suspensions of stable, paramagnetically derivatized or underivatized microbubbles useful for ultrasonic and magnetic resonance imaging and also for therapeutic interventions such as selective tumor destruction.

BACKGROUND OF THE INVENTION

Various technologies exist in which parts of an animal or human body may be imaged so as to aid in diagnosis and therapy of medical disorders. One of techniques that is now widely used in diagnostic imaging various parts of the body is ultrasound. This technique involves the use of an ultrasound transducer to generate and receive sound waves. The transducer is placed on the body surface over an area to be imaged and sound waves generated by the transducer are directed to that area. The transducer then detects sound waves reflected from the underlying area and translates the data into images.

The basis for ultrasound imaging is that, when ultrasonic energy is transmitted through a substance, the acoustic properties of the substance will depend upon the velocity of the transmissions and the density of the substance. Changes in the substance's acoustic properties will be most prominent at the interface of different substances (i.e., solids, liquids and gases). As a consequence, when ultrasound energy is directed through various media, the changes in acoustic properties at such interfaces will change the reflection characteristics, resulting in a more intense sound reflection signal received by the ultrasound transducer.

Early ultrasound techniques suffered from a lack of clarity. As a result, extensive efforts were undertaken to improve the ultrasonic equipment. In addition, contrast agents were introduced into the bloodstream in an effort to obtain enhanced images. Many of these contrast agents were liquids containing microbubbles of gas. These contrast agents themselves are intense sound wave reflectors because of acoustic differences between the liquids and the gas microbubbles enclosed therein. Hence, when these contrast agents are injected into the bloodstream and perfuse the microvasculature of the tissue, clearer images of the tissue may be produced.

A number of different contrast agents are known in the art. For example, Feinstein discloses microbubbles formed from protein solutions, such as those formed from albumin, in U.S. Pat. No. 4,774,958. Microbubbles formed from gelatin are described as suitable contrast agents in U.S. Pat. No. 4,276,885. U.S. Pat. No. 4,684,479 discloses lipid-coated microbubbles which, because of their excellent in vitro stability, were suspected and recently confirmed to be very long-lived in vivo and, hence, are particularly well suited for diagnostic and therapeutic ultrasound applications. The method for preparing the microbubbles disclosed in the '479 patent is not, however, sufficient to allow for the large scale production of medical grade microbubbles.

One of the limitations of diagnostic ultrasound is that it is of very limited use preoperatively in neurosurgical applications because of the presence of bone, and in particular, the skull. Accordingly, magnetic resonance imaging ("MRI"), which is also quite sensitive to tissue pathology, has been rapidly accepted as a technique for neurological diagnosis. MRI of the brain is conducted preoperatively, to provide an image which the surgeon can then consult during an operation.

Initially, MRI was conducted without the aid of a contrast agent. However, the poor specificity of MRI in neurological diseases soon became evident. Contrast agents are now also available to enhance MRI imaging. The best known MRI contrast agents are paramagnetic metal ion chelates with low toxicity. These include manganese, iron and gadolinium metal ions which have been chelated with diethylenetriaminepentaacetic acid or ethylenediaminetetraacetic acid. See, for example, Carr et al, *The Lancet*, 1:484–486 (1984); Runge et al, *Magnetic Resonance Imaging*, 3:27–35 (1985); Lauffer et al, *Magnetic Resonance Imaging*, 3:11–16 (1985); and Lauffer et al, *Magnetic Resonance Imaging*, 3:541–548 (1986).

The foregoing techniques provide medical personnel with the ability to obtain accurate images under a broad range of conditions. There is, however, still a need for a contrast agent which could be-used for both ultrasonic imaging and MRI. For example, while MRI is the method of choice in neurological preoperative diagnosis, real time imaging with MRI during a surgical procedure is not possible. This is because of the massive size of the equipment required for MRI. Yet real time imaging during surgery is often desirable, particularly when the surgeon has reason to believe there has been a shift in position of tissue due to invasion by the surgical procedure and/or change in intracranial pressure. Although ultrasound imaging can be performed during surgery, the current unavailability of a contrast agent which can be used in both ultrasonic imaging and MRI renders anatomical correlation between the preoperative and operative images less reliable.

In addition to diagnostic applications, low frequency ultrasound has also been used therapeutically by physiotherapists to treat a variety conditions. Ultrasound is now also being investigated in the treatment of malignant tumors, through the effects of heat and cavitation. Quan et al, *Phys. Med. Biol.*, 34:1719–1731 (1989) describe a five element ultrasound transducer array potentially useful in the treatment of malignant tumors through the effects of heat. When heat is used in tumor destruction, the tumors are heated to a temperature between 42° and 45° C., producing cellular damage. ter Haar et al, Phys. Med. Biol., 34:1743–1750 (1989), discuss the potential use of high intensity, focused ultrasound in the selective destruction of tumors, without damage to intervening tissues. Heretofore, no one has suggested a method of enhancing the effects of ultrasound through the use of gas-in-liquid microbubbles.

Accordingly, it is an object of the present invention to provide a process from the production of concentrated suspensions of medical grade, lipid-coated microbubbles.

Another object of the present invention is to provide paramagnetically-labeled lipid coated microbubbles suitable for use in ultrasonic imaging and MRI.

A still further object of the present invention is to provide a method for enhancing the selective destruction of tumors by ultrasound through the use of lipid-coated microbubbles.

SUMMARY OF THE INVENTION

These as well as other objects and advantages are achieved in accordance with the present invention, as described hereinafter. In one embodiment, the invention provides methods for the production of underivatized lipid-coated microbubbles suitable for use in medical applications. In another embodiment, the invention provides paramagnetically labeled lipid-coated microbubbles useful in ultrasonic and MRI imaging. In yet another embodiment, the present invention is directed to a novel therapeutic use of the lipid-coated microbubbles in the selective destruction of tumors through the effects of heat and cavitation.

The composition of the lipid-coated microbubbles has previously been described in U.S. Pat. No. 4,684,479. These microbubbles are particularly suited for use in diagnostic and therapeutic medical applications because of their small size and excellent long term stability. When produced in accordance with the improved method described herein, they are small enough to pass through capillaries so as to perfuse tissue. Also, the resulting emulsion is sufficiently free from solid lipid materials and other particulate impurities to be particularly suited for medical applications.

The methods of producing the microbubbles differ from the methods described in the '479 patent, in that the gas-in-liquid emulsion which forms the microbubbles is saline based. In addition, the methods employed herein require the filter sterilization of the emulsion for use in medical applications, to remove particulate and supracolloidal material which otherwise might become lodged in the capillaries during tissue perfusion and cause serious harm. Although filter sterilization is a method step conventionally used for pharmaceutical compositions, in accordance with the present invention, it has surprisingly been found that a very specific filter, having an average pore size of about 0.40 to about 6.0 $\mu$m and having a polysulfone membrane is required to obtain an emulsion suitable as a contrast agent for imaging. Use of other filters, outside the scope of the present invention, results in a large, somewhat variable, statistically significant decrease in microbubble concentration, and hence a decrease in image enhancement, which is unacceptable both on functional grounds and in view of federal regulatory quality-assurance expectations.

Employing the methods of the present invention, microbubbles having a mean diameter of about 2.0 $\mu$m are produced. 99% of the microbubbles are smaller than 4.5 $\mu$m, with 100% being less than 6 $\mu$m.

In another embodiment, the invention provides paramagnetically labelled, lipid-coated microbubbles suitable for use in ultrasonic imaging and MRI. The paramagnetic label is incorporated into the microbubbles by first forming a paramagnetic complex covalently attached to the amino groups of a hydrophobic proteinaceous polymer, such as polyalanine, and then incorporating the complex into the lipid monolayer surrounding the microbubble. The thus-prepared microbubbles can be injected intravenously into an animal or human body, and then detected using conventional ultrasdnic or MRI scanning equipment. The advantage of the derivatized microbubbles is that they permit preoperative microbubble enhanced MRI images of neurological disorders to be clearly correlated anatomically with microbubble enhanced ultrasound images taken during and after neurosurgery. In addition, simultaneous microbubble enhanced MR and ultrasound images can be obtained outside of the brain cavity in order to improve the overall accuracy and information content of the imaging data, e.g., as a cross check for the complete removal of primary tumors and metastases.

In another embodiment, the present invention provides methods for actual therapeutic intervention with lipid-coated microbubbles. Such therapeutic applications include the destruction of tumors by ultrasound heating and/or cavitation of microbubbles at a tumor site. As shown in the examples herein, it has now been demonstrated that underivatized, lipid-coated microbubbles, when injected intravenously into an animal body, will cross disruptions in the blood/brain barrier and thereby pass into tumors in the animal's brain. Accordingly, a selective enhancement of the tumor image is seen during intraoperative ultrasound images of the brain. The demonstrated pooling of the lipid-coated microbubbles at the tumor site in the brain indicates that the tumors can be selectively destroyed through the use of ultrasound, with enhanced destruction of tumor tissue due to the presence of the gas-in-liquid microbubbles present at the site.

BRIEF DESCRIPTION OF THE DRAWINGS

FIG. 4A is an image of rat cerebral glioma several minutes before intravenous injection of the lipid-coated microbubbles; FIG. 4B is an image several minutes after the intravenous injection.

DETAILED DESCRIPTION OF THE INVENTION

Figure 1:
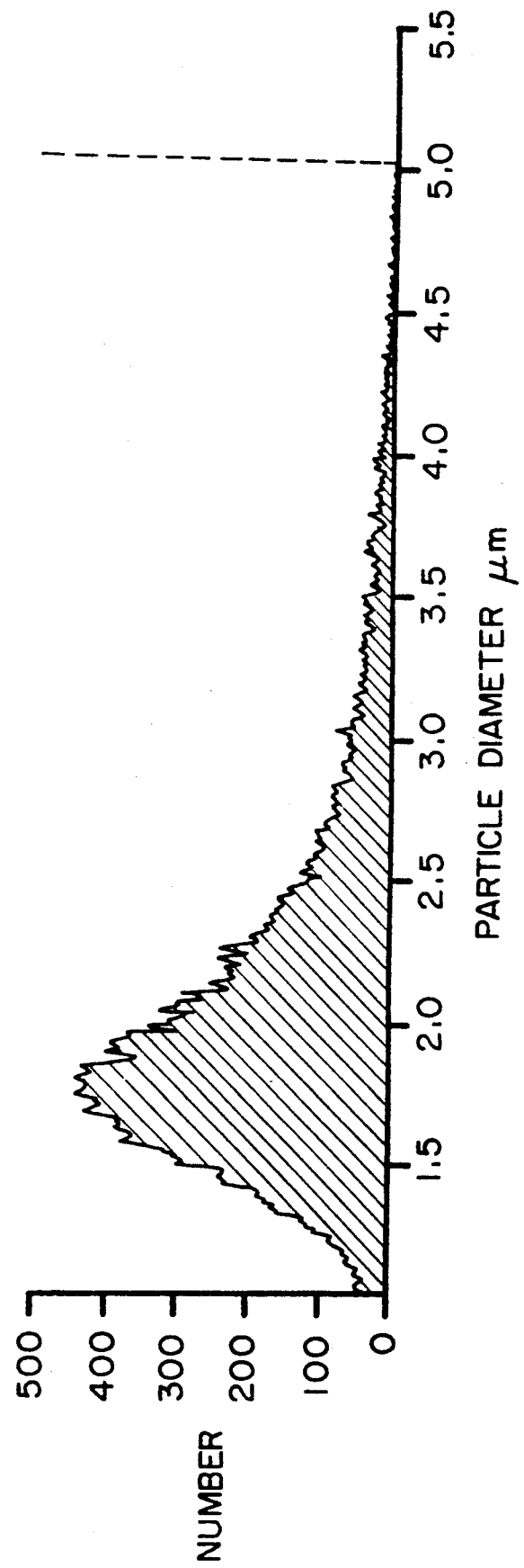
FIG. 1 is a histogram graphically illustrating the particle size distribution of stable lipid-coated microbubbles obtained in accordance with the method of the present invention, as determined by electroimpedance-sensed volumetric sizing.

The surfactant mixtures employed in accordance with the method of the present invention to obtain the underivatized and paramagnetically labeled, lipid-coated microbubbles are best obtained in powdered form. The surfactant mixture is described in detail in U.S. Pat. No. 4,684,479, which is hereby incorporated by reference. Briefly, the surfactant mixture comprises (a) a member selected from the group consisting of glycerol monoesters of saturated carboxylic acids containing from about 10 to about 18 carbon atoms and aliphatic alcohols containing from about 10 to about 18 carbon atoms; (b) a sterol-aromatic acid ester; (c) a member selected from the group consisting of sterols, terpenes, bile acids and alkali metal salts of bile acids; (d) a member selected from the group consisting of sterol esters of aliphatic acids containing from one to about 18 carbon atoms; sterol esters of sugar acids; esters of sugar acids and aliphatic alcohols containing from about 10 to about 18 carbon atoms, esters of sugars and aliphatic acids containing from about 10 to about 18 carbon atoms; sugar acids; saponins; and sapogenins; and (e) a member selected from the group consisting of glycerol, glycerol di or triesters of aliphatic acids containing from about 10 to about 18 carbon atoms and aliphatic alcohols containing from about 10 to about 18 carbon atoms, said components being present in the mixture in a weight ratio of a:b:c:d:e of 2–4:0.5–1.5:0–.5–1.5:0.5–1.5:0–1.5:0–1.5. A more complete description of these components can be found in U.S. Pat. No. 4,684,479. Preferably, the composition is formed from glycerol monolaurate, cholesterol benzoate, cholesterol, cholesterol acetate, and glycerol tripalmitate.

The emulsions are obtained by forming at least a substantially saturated solution of the surfactant mixture in saline based media, which is generally obtained by mixing from about 0.02 to about 0.4 grams of the surfactant mixture with about 100 cc of saline, The resulting mixture is then shaken vigorously for about 2 to about 20 seconds, preferably about 10 seconds in air or other gaseous material at room temperature. After about five minutes, the shaking is repeated two or more times.

Following the shaking, the solution is preferably allowed to stand for about 15 to 60 minutes, most preferably about 30 minutes, to allow the undissolved lipid material to settle out of the solution. Settling out is not essential, but does tend to prevent clogging of the filter during the subsequent filtration step.

The resulting solution is then filtered through a sterile polysulfone membrane filter, having an average pore diameter of from about 40 μm to about 6.0 μm. Preferably, the polysulfone membrane filter will have an average pore diameter of from about 0.40 to about 60 μm and most preferably, about 45 μm. The average pore diameter of the filter used in the filter sterilization step is critical to obtaining a medical grade suspension in accordance with the present invention. Below about 0.40 μm, the filter does not allow sufficient reformation of the microbubbles to obtain suspension useful as an imaging contrast agent. In particular, as the microbubbles (about 1–5 μm in diameter) pass through the filter, they are broken down, and, quite surprisingly, reform after passage through the filter. Reformation of the microbubbles following passage through the filter is believed to be due to the cavitation or turbulence which occurs during passage through the filter. In accordance with the present invention, it has surprisingly been found that this reformation only occurs satisfactorily when a polysulfone membrane filter having an average pore diameter of at least about 0.40 μm is employed.

Use of a filter above about 6.0 μm will allow the passage of particulates approaching the size of red blood cells into the microbubble suspension. This is undesirable because of the increased possibility of complications due to blockage in the circulation system. Preferably, the polysulfone membrane filter will have an average pore diameter of about 0.40 to about 0.60 μm. These preferred filters will allow sufficient reformation of the microbubbles to provide a useful contrast agent, and will also reduce the size of particulates in the suspension, which is most desirable for medical and pharmaceutical applications.

Reformation is particularly enhanced when the filter is a 0.45 μm, sterile polysulfone membrane filter, which has low absorptivity for the microbubbles. Other low absorption materials could similarly be employed. Preferred polysulfone membrane filters are available commercially and can be obtained from Gelman Sciences, Ann Arbor, MI.

The microbubble suspension obtained in accordance with the inventive method remains stable for at least nine months. Typically, the microbubble concentration in the suspension is about 540,000 bubbles ±15% per milliliter. Maximum bubble diameter remains under 6 μm. Particle size analysis is best determined by electroimpedance-sensed volumetric sizing using, for example, a Coulter Multisizer in conjunction with Coulter's AccuComp data handling software. Using this method of analysis, it can be consistently determined that the mean microbubble diameter of the microbubbles produced in accordance with the present invention is about 2 μm. Over 99% of the microbubble population is under 4.5 μm. 100% of the microbubbles are under 6 μm in diameter, which is an ideal limit for contrast agents of this nature.

The paramagnetic complexes that can be employed in accordance with the present invention can be any one of several previously described in the scientific literature for use as contrast agents in MRI. For example, gadolinium ($Gd^{3+}$) or manganese ($Mn^{2+}$) complexed with multidentate ligands, either ethylenediaminetetraacetic acid (EDTA) or diethylenetriaminepentaacetic acid (DTPA) have all previously been used as MRI contrast agents. The Gd-DTPA complex is particularly preferred, since it has been approved by the federal Food and Drug Administration and has been approved for use in humans for the MRI detection of tumors. In addition, the Gd-DTPA complex can readily be attached to the free amine groups of different proteins, which increases the ability of the complex in enhancing MRI 2 to 1 fold. This effect stems from the decrease in molecular motion that occurs upon attachment to a larger molecule. (Lauffer et al, *Magnetic Resonance Imaging*, 3:541–548 (1986).)

In accordance with the present invention, the enhanced MRI contrast can be mimicked and may in fact be further enhanced by the association of the paramagnetic complex with the even larger lipid-coated microbubbles. This association is achieved by first covalently bonding the hydrophilic paramagnetic complex, e.g., Gd-DTPA, to a hydrophobic proteinaceous homopolymer or copolymer, after which the surface-active, paramagnetic Gd-DTPA derivative is associated with the lipid monolayer surrounding the stable microbubbles.

The hydrophobic proteinaceous polymer should be water soluble, to facilitate the synthesis of the paramagnetic surfactant. In addition, it is important that the polymer be moderately hydrophobic, so that it will readily incorporate into the lipid monolayer surrounding the microbubbles. Particularly suitable proteinaceous polymers are moderately hydrophobic, neutral amino acid homopolymers, such as those formed from glycine, valine and alanine and copolymers thereof. Polyalanine, having a molecular weight of about 1000 to 5000 daltons, is particularly preferred.

The method of synthesis of the surface active paramagnetic complex is described in further detail in the examples herein. Preferably, the surface active paramagnetic complex is obtained as a lyophilized powder, which is then incorporated into the lipid monolayer of the microbubbles by adding the derivative to the powdered lipid-surfactant mixture in an amount of about 5-10% w/w. Upon shaking in isotonic saline, the paramagnetic-labeled surface active derivative readily incorporates into the monolayer surrounding the microbubbles, with the paramagnetic label remaining exposed to the aqueous exterior.

The paramagnetically labeled microbubbles of the present invention are useful in the enhancement of both ultrasonic imaging and MRI. The labeled microbubbles will be injected into the human patient or animal intravenously in standard diagnostic doses and then imaged using conventional imaging equipment. These paramagnetically-labeled microbubbles should allow the neurosurgeon to look at, in the operating room using real time ultrasonic imaging, precisely what he or she looked at using MRI preoperatively.

Image mapping procedures can be employed to correlate the ultrasonic and MRI images. Standard image mapping procedures are known and produce maps which allow for the reconstruction of an ultrasound image from the lesion's actual size and shape. See, for example, Le Roux et al, *Neurosurg.*, 71:691-698 (1989). Image mapping procedures may also involve a mapping from the tumor histology to the MRI image. Using composition or direct mapping, the relationship between the MRI and ultrasonic images can be established.

In another embodiment of the present invention, there is provided a method for enhancing the selective destruction of tumors using the heating and cavitational effects of ultrasound. This method takes advantage of the tendency of the medical-grade lipid microbubbles to pool or concentrate in tumors and the established fact that gas pockets, such as those provided by the microbubbles, are known to act as heat sinks as well as cavitation nuclei. For example, this inventor has recently found that the lipid-coated microbubbles of the present invention will, in fact, cross into and intensify ultrasonic images of tumors in the rat brain. Passage of the ultrasmall lipid microbubbles is possible primarily because of the alterations in capillary permeability and vascular structure in the area of the tumor. These pathological alterations in intrinsic tumor capillaries increase the likelihood for small particulate matter to pass out of circulation into the cerebral tumor. Virtually all classes of tumors are known to have similar disruptions in the vascular endothelium, regardless of the site of the tumor. Similarly, the lipid-coated microbubbles cross the vascular endothelium into tumors elsewhere in the body as they do in the brain.

It has previously been shown that ultrasound, in the absence of any contrast agent, can be utilized therapeutically in the selective destruction of tumor tissue. (Quan et al, *Phys. Med. Biol.*, 34:1719-1731 (1989); ter Haar et al, *Phys. Med. Biol.*, 34:1743-1750 (1989).) In accordance with a third embodiment of the invention, the known cavitational and heating effects of ultrasound may be enhanced through the use of lipid-coated microbubbles which have pooled at the tumor site.

The novel method involves intravenously injecting lipid-coated microbubbles into a human or animal in order for the microbubbles to accumulate or pool at a predetermined area which has been ultrasonically scanned to obtain a diagnostic, confirmatory image of the tumor area and then intensifying the ultrasound signal, thereby providing a therapeutic heating and/or cavitational effect.

The excellent uniformity and extremely small size, coupled with the exceptional in vivo longevity of the lipid-coated microbubbles enables them to: 1) safely traverse the pulmonary microcirculation, and 2) endure passage across structural disruptions of the vascular lining (or wall), as commonly occurs in the abnormal capillary beds of many types of tumors. The resulting accumulation and persistence of these lipid-coated microbubbles at the tumor site directly causes a selective enhancement of the ultrasonographic image of the tumor, as observed in Example 6 herein with brain tumors at this microbubble dosage level. The selective image enhancement is best displayed by taking ultrasound scans of the tumor site before and again a few minutes after microbubble contrast injection intravenously.

This selective accumulation of lipid-coated microbubbles at the tumor site can be very useful for accentuating the following tw therapeutic effects of ultrasound on tumors. First, the ability to focus ultrasound precisely on a predetermined volume (e.g., specified from prior diagnostic imaging) provides the ability to selectively destroy tissue at a tumor site without damage to intervening tissues. The highly echogenic nature of the ultrasonic lesions produced during in vivo studies and in excised liver samples in vitro suggest the effect is produced by cavitation damage. The extent of the ultrasonic lesion is dependent upon both length and intensity of the focused ultrasound exposure, where the intensity of the focused ultrasound is routinely higher than that required simply for imaging (ter Haar et al, *Phys. Med. Biol.*, 34:1743-1750 (1989)). However, lower intensities of ultrasound can still be effective for tumor therapy through its thermal effect on tissue. Ultrasound in the low megahertz frequency range is used to treat malignant tumors by heating them to temperatures between 42° and 45° C., producing cellular damage, the extent of which is determined by the duration and number of treatments (Quan et al, *Phys. Med. Biol.*, 34:1719-1731 (1989)). Both the cavitational and thermal mechanisms of ultrasonic tumor therapy can be accentuated by the presence of the accumulated microbubbles in the tumor, since microbubbles are known to serve very effectively as cavitation nuclei (D'Arrigo, *J. Chem. Phys.*, 71:1809-1813 (1979); ibid., 72:5133-5138 (1980); ibid., 75:962-968 (1981)) and their contained gas readily provides a local source of heat generation in an ultrasonic field.

Considering first the cavitation facilitation, the threshold for macroscopic bubble formation in an ultrasonic field has been reported to be similar in both agar gels (ter Haar et al, *Phys. Med. Biol.*, 34:1533-1542) and guinea pig hind legs (Daniels & Ter Haar, *Proc. I.O.A.*, 8:147-157). At the same time, it is also known from extensive physicochemical experimentation with highly purified gels that the ordinary cavitation threshold for macroscopic bubble formation in aqueous-based gels can be lowered drastically by the presence of moderate or even low concentrations of stable microbubbles (D'Arrigo, *Aviat. Space Environ. Med.*, 49:358-361; D'Arrigo, J. Chem. Phvs., 71:1809-1813 (1979); ibid., 72:5133-5138 (1980); ibid., 75:962-968 (1981)). As concerns the thermal enhancement effect mediated by any accumulated microbubbles in the tumor, this physical relationship stems from the fact that free gas bubbles in a liquid are capable of strong oscillatory motion (i.e., small amplitude, radial pulsations of the bubbles) in an ultrasound field (Ophir & Parker, *Ultrasound Med. Biol.*, 15:319-333 (1989). This strong oscillatory motion of the microbubbles provides a mechanism for local heat generation in the region of the microbubble. The degree of non-linearity in the ultrasound beam will also determine the temperature rise achieved. Theory predicts more non-linear distortion for ultrasonic pulses with higher peak positive pressure amplitudes. Associated with this, there may be an enhancement of the predicted temperature rise due to absorption of the higher harmonic components (Swindell, *Ultrasound Med. Biol.*, 11:121-130).

Following microbubble-assisted ultrasonic destruction of a tumor site, the walls of the tissue cavity created by liquefaction and drainage of the ultrasonic lesion site can be better defined with use of more lipid-coated microbubble contrast and the progress of resolution of this cavity can be tracked over time.

The ultrasound frequency and exposure time are parameters which will have to be controlled in order to achieve the desired tumor destruction. These parameters will, in turn, be dependent upon a number of factors, including the size and location of the tumor and the ultrasonic equipment used. In general, at constant intensity, the longer the exposure time, the greater the extent of tumor tissue damage. Similarly, if the intensity is increased at constant exposure time, the extent of damage will again be increased.

Another therapeutic application for the medical grade microbubbles produced in accordance with the method of the present invention involves the targeted delivery of therapeutic compositions, such as drugs and chemotherapeutic agents, to the tumor site. This intervention also takes advantage of the natural tendency of the lipid-coated microbubbles to pool in the tumor tissue. In this application, cytotoxic agents are entrapped within the membrane shell of the lipid-coated microbubbles, and are released upon injection of the microbubbles into the body and the application of high intensity ultrasound waves at the tumor site. Based upon the known effects of ultrasound, the energy will cause the microbubbles to burst at the site, thereby releasing the cytotoxic agent directly at the tumor location.

The incorporation of the particulate, cytotoxic agent within the membrane of the lipid-coated microbubbles can be approached in any one of a number of ways. One approach involves the preparation of a hydrophobic coating that is applied to the surface of the particulate form of a cytotoxic agent. The thus-coated cytotoxic agent is then introduced as an aerosol over or otherwise deposited on the surface of a saturated solution of an appropriate lipid surfactant mixture in a closed container. Vigorous shaking by hand then traps macroscopic gas pockets, containing either the particulate aerosol or particle adhering to the gas/liquid interface, within the body of the aqueous lipid surfactant solution. Thereafter, the macroscopic gas pockets shrink by gas dissolution, and a tightly packed, lipid-surfactant monolayer forms around the microbubbles, which have entrapped therein the hydrophobically coated, cytotoxic drug particles.

The following examples further illustrate the present invention. Unless otherwise stated, all percentages are by weight.

EXAMPLE 1

This example illustrates the preparation of a surfactant mixture for use in accordance with the present invention. A surfactant mixture was prepared in accordance with the present invention by admixing glycerol monolaurate, cholesterol benzoate, cholesterol, cholesterol acetate and glycerol tripalmitate in a weight ratio of 3:1:1:1:1, respectively, to obtain a dry powdery surfactant mixture.

EXAMPLE 2

This example illustrates the method for production of medical grade lipid-coated microbubbles. Saline solution was prepared by dissolving ACS reagent grade NaCl (0.9% w/v) in distilled water. The thus prepared solution was then filtered through a sterile 0.2 μm membrane filter.

An excess (1.5 gm/liter) of the powdered lipid-surfactant mixture prepared as in Example 1 was added to the above solution. The resulting solution was shaken vigorously (mechanically; sonication is unnecessary) for 10 seconds in air at room temperature. After five minutes, this shaking step was repeated two more times. The undissolved lipid material was then allowed to settle out for about 30 minutes and the resulting colloidal suspension (i.e., supernatant) was filtered through a sterile polysulfone membrane 0.45 μm pore-diameter, low-absorption membrane filter (Gelman Sciences, Ann Arbor, MI).

The resulting suspension of lipid-coated microbubbles was then analyzed using a Coulter Multisizer in conjunction with Coulter's AccuCorp Software (Coulter Electronics, Inc., Hialeah, FL). Analysis was conducted in isotonic saline at approximately 21° C. The results of this analysis are set forth in FIG. 1. The analysis revealed microbubbles present in a concentration of about 540,000 bubbles/ml. Mean microbubble diameter was 2.00 μm and greater than 99% of the microbubbles were below 4.35 μm.

COMPARATIVE EXAMPLE 3

This example illustrates the criticality of using a filter having an average pore size of at least about 0.40 μm and polysulfone membrane, by comparing the microbubble suspension formed in accordance with the present invention with a suspension prepared using a 20 μm pore size filter and a cellulose-ester membrane filter, respectively.

Filter size

Figure 2:
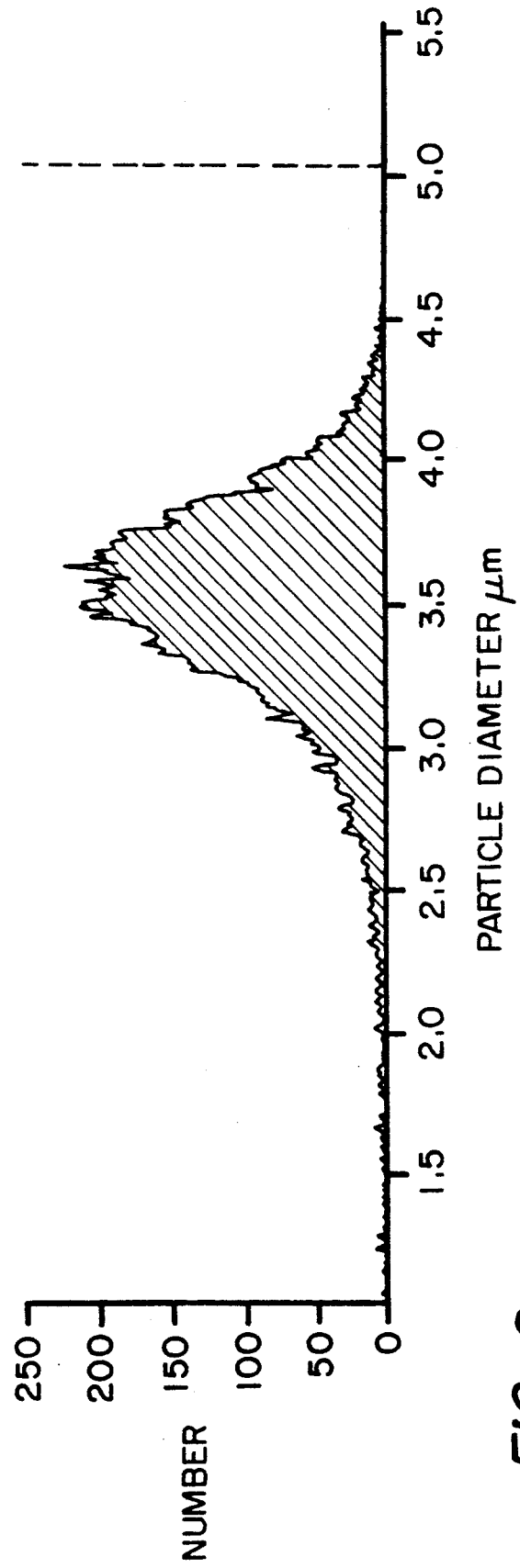
FIG. 2 is a histogram graphically illustrating the particle size distribution of a lipid-coated microbubble suspension prepared using a 0.20 $\mu$m filter, as determined in FIG. 1.

A saturated solution of a surfactant mixture was prepared in accordance with Example 2, except that a 0.20 μm polysulfone membrane filter was used in the filtration step instead of a 0.45 μm polysulfone membrane filter. Particle size analysis was conducted as in Example 2. The results of the analysis are set forth in FIG. 2.

As can be seen from the analysis, while the size distribution remained between 1-5 μm in diameter, the microbubble concentration dropped precipitously to about 210,160 microbubbles per ml., or about 40% of the concentration obtained in accordance with the present invention. This suggests that the 0.20 μm filter does not allow sufficient reformation of the microbubbles after passage through the filter.

The suspension obtained using the 0.20 μm polysulfone membrane filter is very unsatisfactory as a contrast agent, in view of the low concentration of microbubbles present therein and the variability of microbubble concentration measured. The product specifications developed for this medical-grade contrast agent, in accord with federal regulatory quality-assurance expectations, require a concentration of 540,000±15% microbubbles/ml —which obviously cannot be met in this case.

Composition

Figure 3:
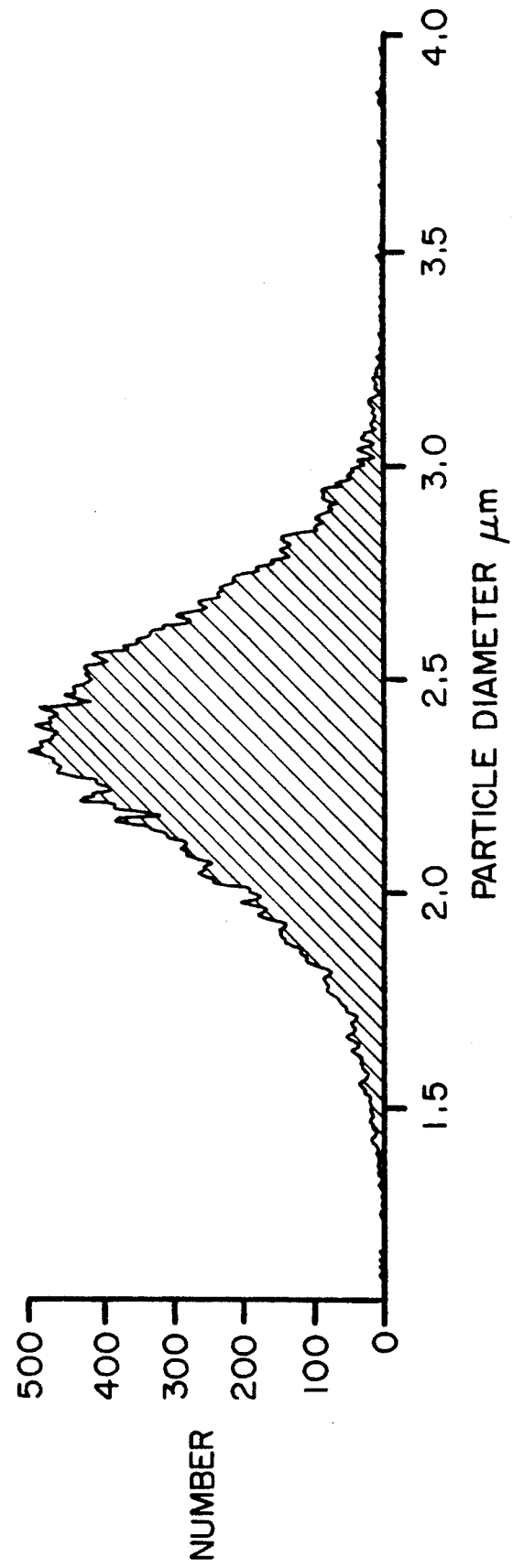
FIG. 3 is a histogram graphically illustrating the particle size distribution of a suspension of lipid-coated microbubbles prepared using a 0.45 $\mu$m cellulose-ester membrane filter as also determined in FIG. 1.

The composition of the filter employed in the second filtration step is also an important aspect of the present invention, although the composition is not as critical as filter pore size. A saturated solution of a surfactant mixture was next prepared in accordance with Example 2, except that a 0.45 μm cellulose acetate/cellulose nitrate membrane filter was utilized rather than the preferred 0.45 μm polysulfone (low-absorption) membrane filter. Particle size analysis was conducted as in Example 2. The results of the analysis are set forth in FIG. 3.

As can be seen from this analysis, the size distribution of the microbubbles again remains at about 1-5 μm in diameter. However, the microbubble concentration dropped to about 441,740 microbubbles per ml of suspension. This is approximately 19% lower than the concentration of microbubbles obtained in accordance with the present invention, which employs a polysulfone membrane filter. Such a reduction is sufficient to seriously limit the suspension's usefulness as a sonographic contrast agent. Other membrane filter materials, such as PTFE, lead to even poorer suspension quality.

EXAMPLE 4

This example illustrates the method of preparing paramagnetically labeled, lipid-coated microbubbles obtained in accordance with the present invention.

Fifteen grams of polyalanine (1000-5000 daltons mol. wt.) were dissolved in 2500 ml of 1.0 M phosphate buffer and filtered through a 0.5 μm pore-diameter filter. A 20-fold molar excess of solid DTPA (Sigma Chemical Co., St. Louis, MO) was added to the protein solution, and the pH adjusted to pH 8 by addition of solid sodium phosphate buffer. After 30 minutes of additional stirring, the pH was adjusted to pH 5.6 with glacial acetic acid (or concentrated HCl) and a 30-fold molar excess of $GdCl_3$ (Aldrich Chemical Co., Milwaukee, WI) to protein was added. The solution was then dialyzed against 0.15 M saline at 5° C. for 96 hours using 1000-dalton cut-off dialysis tubing. The resulting 1.8-2.0 liters of solution was then lyophilized over several days to give the white, solid derivative (approximately 20 gm).

Incorporation of the lyophilized Gd-DTPA derivative into lipid-coated microbubbles was accomplished by adding the derivative (5-10% w/w) to the powdered lipid-surfactant mixture of Example 1. Upon shaking in the isotonic saline, the paramagnetic-labeled surface-active derivative is incorporated into the microbubble's surrounding lipid monolayer, with the Gd-DTPA label remaining exposed to the aqueous exterior. Additional Gd-DTPA derivative may remain dissolved in the isotonic saline, and co-exist with the lipid-coated microbubbles.

EXAMPLE 5

This example illustrates that the paramagnetic-labeled and/or unlabeled lipid-coated microbubbles, produced by the above-described process, are generally safe for medical diagnostic and therapeutic applications.

Six Sprague-Dawley male rats were given an intravenous infusion of lipid coated microbubbles produced in accordance with Example 1 at an average dosage of 0.14 ml/kg 3 times weekly for 6 weeks. Blood samples were obtained at 2 and 6 weeks for a serum chemistry profile of 19 parameters including total protein, LDH, cholesterol and creatinine. At the conclusion the animals were sacrificed, subjected to a gross autopsy, organ weights obtained for 7 critical organs and the tissues fixed for histological examination.

A comparison of the 6 week versus 2 week chemistry values show some differences and elevations in a number of the parameters examined, with the most prominent difference occurring in the LDH values. The gross and microscopic pathology examinations did not reveal any lesions related to the administration of the test material. Furthermore, there were no atheromata, mural thrombi or emboli seen in any of the tissues examined. These results support the safety of the lipid-coated microbubbles produced in accordance with the method of the present invention for single or double administration for clinical trial.

Thereafter, three "SPF" (New Zealand albino) male rabbits received an intravenous infusion of the lipid-coated microbubbles three times per week for 2 ½ weeks at a dosage of 0.48 ml/kg. After the initial 2 ½ week period, lipid-coated microbubbles (0.48 ml/kg) with added Gd-DTPA derivative (3-20 mg/kg) were continued at the same dosage for 2.5 months. An extensive serum chemistry profile, a hematology profile and four coagulation tests were performed on blood samples taken: prior to injection, after 2.5 weeks, 7 weeks, and 11 weeks after the initial injection, and prior to necropsy. At the end of this period the animals were sacrificed, subjected to a gross autopsy and tissues fixed for histological examination.

The clinical pathology parameters for serum chemistry, hematology and coagulation revealed no findings that could be related to the administration of the test material and were essentially within normal limits at each examination period. The microscopic pathology examination revealed no atheromati, mural thrombi or emboli or any other findings that could be related to the administration of the paramagnetically-labeled lipid-coated microbubbles. Therefore, the derivatized suspension is safe for single or 2 times administration in short term clinical trials.

EXAMPLE 6

This example demonstrates that the lipid-coated microbubbles prepared in accordance with the present invention will cross into and intensify the ultrasonic images of glioma tumors in the rat brain.

Lipid-coated microbubbles were prepared in accordance with Example 2 and supplied in a concentration of 520,000-550,000 microbubbles per ml in isotonic saline.

Bilateral craniectomies were performed on Sprague-Dawley 250-333 g male rats. The mice were anesthetized with ketamine (90mg/kg), supplemented with xylazine (10mg/kg). Using the coordinates from the stereotaxic atlas of Pelligrino et al (*A Stereotaxic Atlas of the Rat Brain*, N.Y., Plenum (1979)) for a deep brain parenchymal target, a needle was introduced for direct injection of 0.1 ml of isotonic saline containing $3 \times 10^6$ cultured C-6 glioma cells. This procedure provided a dense, subcortical, circumscribed tumor which remained intraparenchymal, with no spill into the ventricles or the subarachnoid space. The lesion was easily detected by histological evaluation. Histological evaluation showed a consistent progression in tumor size over time.

20 rats were given the intra-parenchymal injection of cultured glioma cells, as described above and 11 of these rats received a daily intravenous injection (via tail vein) of 0.05 ml of the lipid-coated microbubbles. Ultrasound imaging was performed using a 7.5 MHz probe and images were recorded on a broadcast-grade videotape recorder and subsequently transformed to image processing software. The day of sonographic detection of the developing cerebral glioma in each animal was recorded; the mean and S.E.M. were calculated for the microbubble (n=11) and control (n=9) groups.

All animals were sacrificed after the last image was taken and brains were removed for histological sectioning to verify tumor location and to determine actual tumor size.

Figure 4A:
FIGS. 4A and 4B are representative ultrasound images showing that the lipid-coated microbubbles will cross into and intensify the ultrasonic image of gliomas in a rat brain.
Figure 4B:
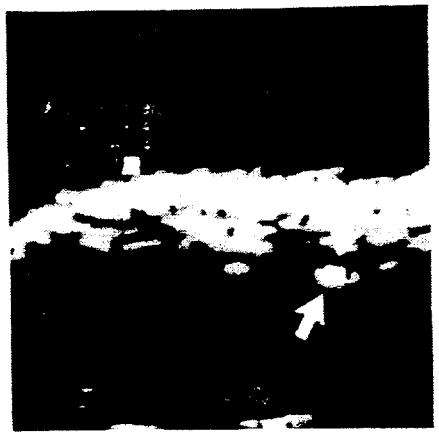

FIG. 4 is a representative ultrasound image of a rat cerebral glioma before (4A) and within a few minutes after intravenous injection of the lipid-coated microbubbles (4B). The results of the experiments showed that the lipid-coated microbubbles will cross into the gliomas in the rat brain and intensify the ultrasonic image obtained. The results of the experiment, set forth in Table 1 below, also show that the developing tumors can be detected earlier when the microbubble contrast agent is employed, compared to the control group.

TABLE 1

| First Sonographic Detection of Brain Tumors (Days) | |
|---|---|
| Control (n = 9) | Microbubble (n = 11) |
| 6 | 4 |
| 8 | 5 |
| 6 | 4 |
| 9 | 4 |
| 6 | 4 |
| 6 | 4 |
| 7 | 4 |
| 6 | 4 |
| 6 | 4 |
| | 4 |
| | 4 |
| Mean 6.67 | 4.09 |
| ± | |
| S.E.M. 0.35 | 0.08 |

$p < .001$ $(F_{18}^1 = 54.19)$

This Table lists, for each animal, the time necessary for first sonographic detection of the developing cerebral glioma. The means of 6.67±0.35 and 4.09±0.08 represent the mean time (±S.E.M.) for the separate control and microbubble groups, respectively. Sonographic detection of the cerebral gliomas appeared about 40% earlier in the rats injected with the lipid-coated microbubbles than in the control group, which further indicates the clinical potential of the lipid-coated microbubbles.

What is claimed is:

1. A method for preparing an imaging about suitable for enhancement of ultrasonic imaging and magnetic resonance imaging comprising the steps of:
    A. obtaining a moderately hydrophobic neutral amino acid homopolymer or copolymer which is capable of readily incorporating into a lipid monolayer, and is labeled with a paramagnetic complex comprising a metal ion and organic chelating ligand;
    B. dissolving the labeled, hydrophobic polymer in a saline solution in an amount of about 10 mM;
    C. adding a surfactant mixture comprising:
        (a) a member selected from the group consisting of glycerol monoesters of saturated carboxylic acids containing from about 10 to about 18 carbon atoms and aliphatic alcohols containing from about 10 to about 18 carbon atoms;
        (b) a sterol-aromatic acid ester;
        (c) a member selected from the group consisting of sterols, terpenes, bile acids and alkali metal salts of bile acids;
        (d) a member selected from the group consisting of sterol esters of aliphatic acids containing from one to about 18 carbon atoms; sterol esters of sugar acids; esters of sugar acids and aliphatic alcohols containing from about 10 to about 18 carbon atoms, esters of sugars and aliphatic acids containing from about 10 to about 18 carbon atoms; sugar acids, saponins; and sapogenins; and
        (e) a member selected from the group consisting of glycerol, glycerol di or triesters of aliphatic acids containing from about 10 to about 18 carbon atoms and aliphatic alcohols containing from about 10 to about 18 carbon atoms;
    D. shaking said solution mechanically for from about 2 to about 10 seconds in gaseous atmosphere at room temperature, thereby forming a concentrated gas-in-liquid emulsion; and
    E. passing the solution obtained after step (D) through a sterile polysulfone membrane filter having an average pore diameter of about 0.40-6.0 μm.

2. A method according to claim 1, further comprising the steps of allowing undissolved lipid materials to settle out for a period of about 15-60 minutes before passing the solution through the polysulfone membrane filter.

3. A method according to claim 2, wherein the sterile polysulfone membrane filter has an average pore diameter of about 0.40-0.60 μm.

4. A method according to claim 3, wherein the sterile polysulfone membrane filter has an average pore diameter of about 45 μm.

5. A method according to claim 3, wherein the moderately hydrophobic polymer is selected from the group consisting of homopolymers of valine, glycine and alanine and copolymers thereof.

6. A method according to claim 5, wherein the paramagnetic complex is selected from the group consisting of gadolinium DTPA, manganese DTPA, gadolinium EDTA and manganese EDTA.

7. A method according to claim 6 wherein the paramagnetic complex is gadolinium DTPA.

8. A method according to claim 7, wherein the surfactant mixture components are present in the surfactant mixture in a weight ratio a:b:c:d:e of about 2-4:0-.5-1.5:0.5-1.5:0.5-1.5:0-1.5.

9. A method according to claim 8, wherein the surfactant mixture consists essentially of glycerol monolaurate, cholesterol benzoate, cholesterol, cholesterol acetate and glycerol tripalmitate in a weight ratio of 2-4:1:1:1:1.

10. A method according to claim 1, further comprising the steps of mechanically shaking the solution at least two more times before passing the solution through the polysulfone membrane filter.

* * * * *

UNITED STATES PATENT AND TRADEMARK OFFICE
CERTIFICATE OF CORRECTION

PATENT NO. : 5,215,680

DATED : June 1, 1993

INVENTOR(S) : Joseph S. D'Arrigo

It is certified that error appears in the above-identified patent and that said Letters Patent is hereby corrected as shown below:

```
Column 13, line 58:
In Claim 1, line 1, "about" should read --agent--.
Column 14, line 42:
In Claim 4, line 3, "45" should read --.45--.
```

Signed and Sealed this

Tenth Day of May, 1994

*Attest:*

BRUCE LEHMAN

*Attesting Officer*  *Commissioner of Patents and Trademarks*